United States Patent [19]

Sgro

[11] Patent Number: 5,735,871
[45] Date of Patent: Apr. 7, 1998

[54] SELF-EXPANDING ENDOPROSTHESIS

[76] Inventor: Jean-Claude Sgro, 42 cours Général de Gaulle, 21000 Dijon, France

[21] Appl. No.: 568,258

[22] Filed: Dec. 6, 1995

[30] Foreign Application Priority Data

Dec. 9, 1994 [FR] France .................................. 94 15085

[51] Int. Cl.$^6$ ............................................. A61M 29/00
[52] U.S. Cl. ................................. 606/198; 606/194
[58] Field of Search ................................ 606/191, 192, 606/194, 195, 198; 623/1, 12

[56] References Cited

U.S. PATENT DOCUMENTS

| 5,007,926 | 4/1991 | Derbyshire | 606/194 |
|---|---|---|---|
| 5,211,658 | 5/1993 | Clouse | 606/198 |
| 5,292,331 | 3/1994 | Boneau | 606/198 |
| 5,354,308 | 10/1994 | Simon et al. | 606/198 |
| 5,449,373 | 9/1995 | Pinchasik et al. | 606/198 |
| 5,496,365 | 3/1996 | Sgro | 606/191 |
| 5,514,154 | 5/1996 | Lau et al. | 606/194 |
| 5,549,635 | 8/1996 | Solar | 606/198 |

FOREIGN PATENT DOCUMENTS

| 1205743 | 9/1970 | United Kingdom . |
|---|---|---|
| 93/06883 | 4/1993 | WIPO . |

OTHER PUBLICATIONS

Copy of French Search Report dated Aug. 22, 1995.
Abstract of DE-A-34 17 738; Nov. 1985.
Abstract of EP-A-0 566 807; Oct. 1993.

Primary Examiner—Michael Buiz
Assistant Examiner—Patrick W. Rasche
Attorney, Agent, or Firm—Ostrolenk, Faber, Gerb & Soffen, LLP

[57] ABSTRACT

The present invention relates to a self-expanding endoprosthesis intended to support walls of anatomical channels. The endoprosthesis according to the invention comprises 2n external longitudinal elements, and 2n other intermediate longitudinal elements, distributed in a parallel arrangement about the axis of the endoprosthesis, and offset with respect to one another along the axis, and a plurality of rings distributed about the axis of the endoprosthesis, joining the longitudinal elements and each being in the form of a filament of zigzag configuration. According to the invention, the folded-down configuration of the endoprosthesis is obtained by longitudinal traction of the external elements with respect to the intermediate elements.

10 Claims, 3 Drawing Sheets

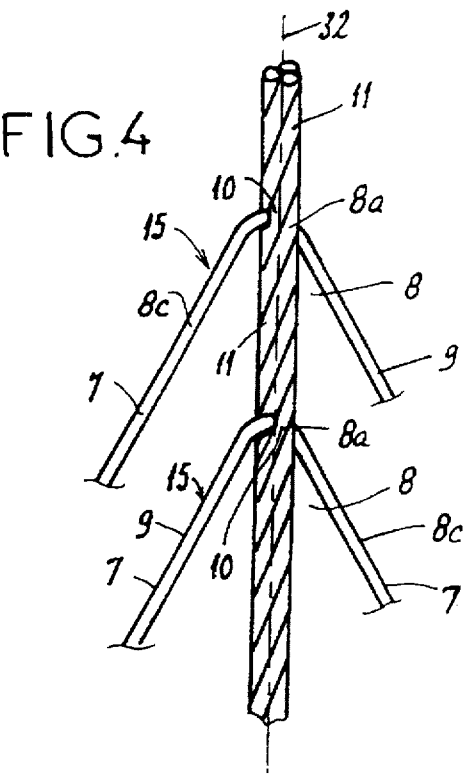
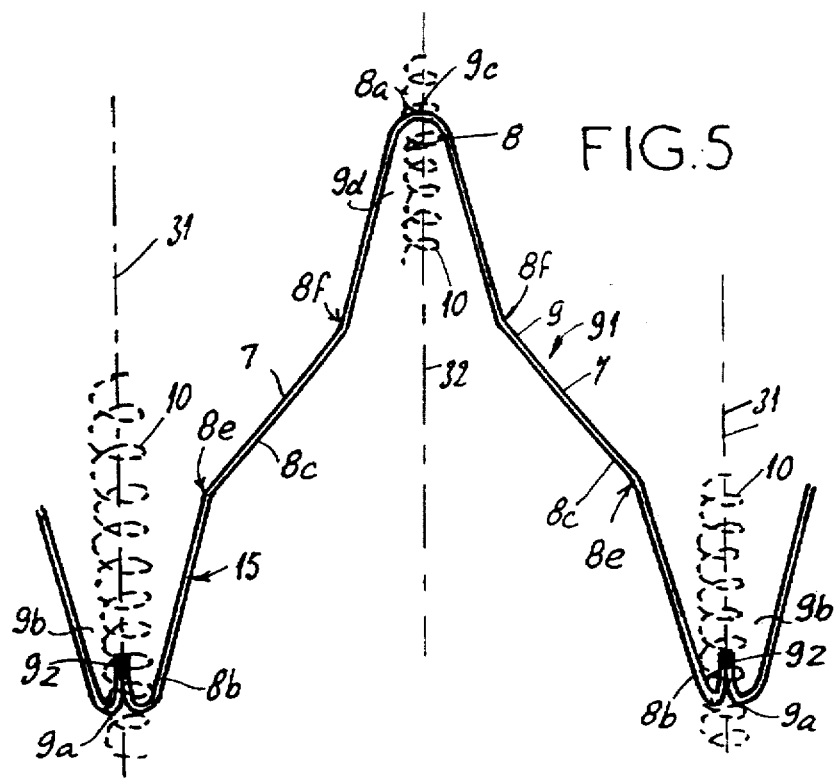

SELF-EXPANDING ENDOPROSTHESIS

BACKGROUND OF THE INVENTION

The present invention relates to a self-expanding endoprosthesis, that is to say a prosthesis or device, of a generally tubular form, which is intended to be introduced into and positioned within the lumen of any anatomical channel or conduit of the human body or animal body, in such a way as to re-establish or maintain the normal and transverse dimensions of said lumen, for example in order to re-establish or maintain the passage of a fluid through said channel or conduit.

DESCRIPTION OF THE PRIOR ART

Endoluminal prostheses of this type are well known in medical practice, in the fields of vascular, biliary or intestinal surgery, and are often designated by the term "stent".

In accordance with U.S. Pat. No. 5,496,365 and EP-A-0, 566,807, a self-expanding endoprosthesis of monobloc or monolithic construction has been described and proposed, said endoprosthesis having a generally cylindrical form, being of openwork design, and forming an internal lumen. In a general manner, this endoprosthesis is capable of assuming two configurations, namely one in which it is folded-down counter to an inherent centrifugal force of elastic return, resulting from the construction defined hereinafter, in which the internal lumen exhibits a relatively small diameter, and the other in which it is deployed, this being obtained by release under the effect of this same centrifugal force, in which the above-mentioned internal lumen exhibits a relatively large diameter.

This monobloc and openwork endoprosthesis comprises:

2n longitudinal elements, called external shafts, distributed in a parallel arrangement about the axis of the endoprosthesis;

2n other longitudinal elements, called intermediate shafts, distributed in a parallel arrangement about the axis of the endoprosthesis, between the external longitudinal elements, or external shafts, n being an integer;

the intermediate elements or shafts being offset longitudinally with respect to the external longitudinal elements or shafts by the same predetermined distance, in such a way that, at each end of the endoprosthesis, the extremities of the intermediate elements are included in a radial plane (this being perpendicular to the axis of the endoprosthesis) separated by said predetermined distance from the radial plane including the adjacent extremities of the external elements;

a plurality of rings, isolated as represented in FIG. 10 of the document EP-A-0,566,807, distributed along the axis of the endoprosthesis, joining the external and intermediate longitudinal elements or shafts to one another; each ring comprises, along its cylindrical developed surface, 2n transverse strands connected continuously to one another, forming, in pairs, n chevrons whose vertices are linked respectively to the intermediate elements or shafts, and the extremities of the arms are linked respectively to the external elements or shafts; the chevrons of the various rings are respectively all oriented in the same direction, in such a way that an intermediate longitudinal element or shaft and all the transverse strands which are connected to it on either side together exhibit the shape of a fish bone.

By virtue of the structure or construction described above, the folded-down configuration of the endoprosthesis is obtained by longitudinal traction of the external elements or shafts, with respect to the intermediate elements or shafts, in the direction of the axis of the endoprosthesis.

SUMMARY OF THE INVENTION

The subject of the present invention is an embodiment of the endoprosthesis defined above in a general manner, conferring upon the latter great flexibility on either side of its axis, allowing it to adapt without difficulty to the various shapes or angles of the anatomical conduits or channels of the human body or animal body. Moreover, the embodiment sought must not compromise the mechanical stability or strength of the endoprosthesis, and in particular there should be no weak points in said endoprosthesis.

According to the present invention, the following practical features are retained.

On the one hand, the various rings are distinct from one another, and from the external and intermediate longitudinal elements, and in each case comprise transverse strands, together exhibiting the form of an essentially continuous and closed filament, of zigzag configuration, and included in an imaginary envelope, for example a cylindrical one; the vertices of the salient and reentrant angles of the various rings of zigzag configuration are aligned respectively along external and intermediate imaginary lines which are parallel to the axis of the endoprosthesis. Moreover, on the other hand, at least some of the external and intermediate longitudinal elements are flexible, filiform elements intersecting with the filaments of the various rings respectively, at the site of the external and/or intermediate imaginary lines; and said flexible, filiform elements and/or the filaments of the various rings are designed to be linked to one another in position, at the site of their respective intersections.

BRIEF DESCRIPTION OF THE DRAWINGS

The present invention is now described with reference to the attached drawing, in which:

FIG. 4 represents a partial side view of the endoprosthesis represented in FIGS. 1 through 3;

FIG. 5 represents a partial view, in development, from the side, of a ring belonging to the prosthesis according to FIGS. 1 through 4;

DESCRIPTION OF THE PREFERRED EMBODIMENTS

Figure 1:
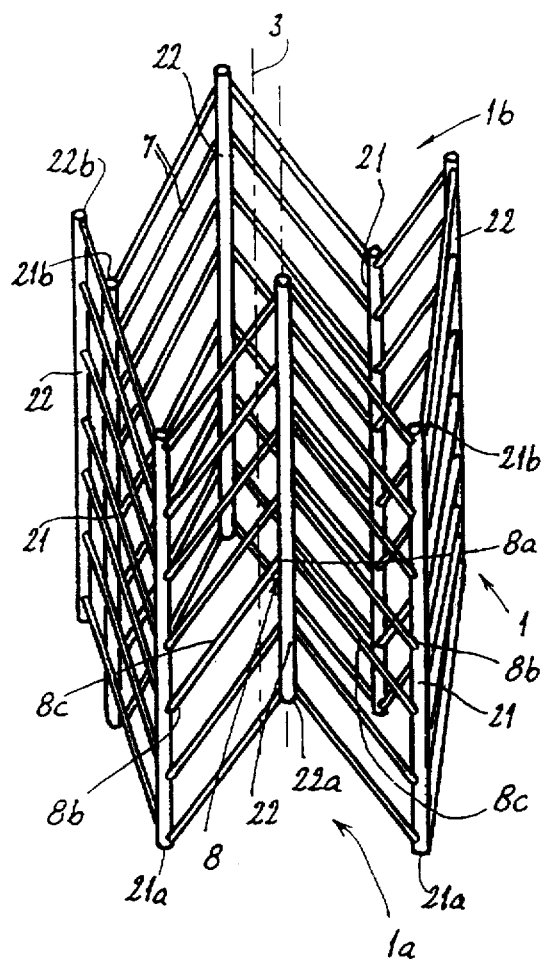
FIG. 1 represents an endoprosthesis according to the present invention, in a perspective view, and in a deployed configuration.
Figure 2:
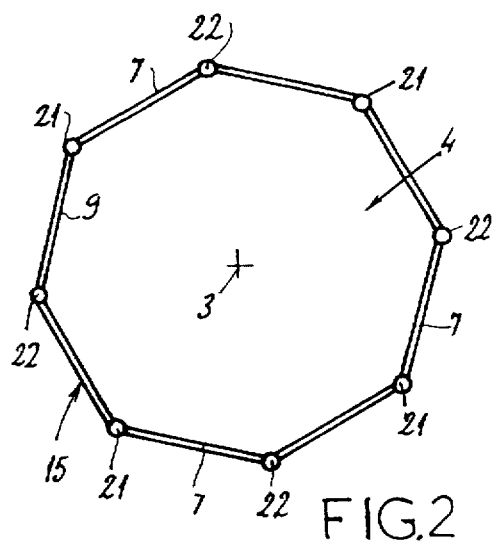
FIG. 2 represents a plan view of the endoprosthesis represented in FIG. 1.

In accordance with FIGS. 1 through 5 and according to a first embodiment of the invention, a self-expanding endoprosthesis I according to the invention does not have a monobloc or monolithic construction, since it consists in a general manner of various rings 15 which are coaxial with the axis 3 of the endoprosthesis and which are separate from one another, and of flexible and filiform longitudinal elements which are separate from the rings 15, and among which a distinction may be made, for the purposes of the description, between external elements 21 and intermediate elements 22.

More specifically, the endoprosthesis 1 comprises:

2n external longitudinal elements 21, distributed in a parallel arrangement about the axis 3 of the endoprosthesis;

2n other intermediate longitudinal elements 22, distributed in a parallel arrangement about the axis 3 of the endoprosthesis, and disposed between the external elements 21, n being an integer, for example equal to 4 in the case of the representation in FIGS. 1 through 5;

a plurality of rings 15 distributed about the axis 3 of the endoprosthesis, joining or connecting the external longitudinal elements 21 and the intermediate longitudinal elements 22 to one another.

Figure 3:
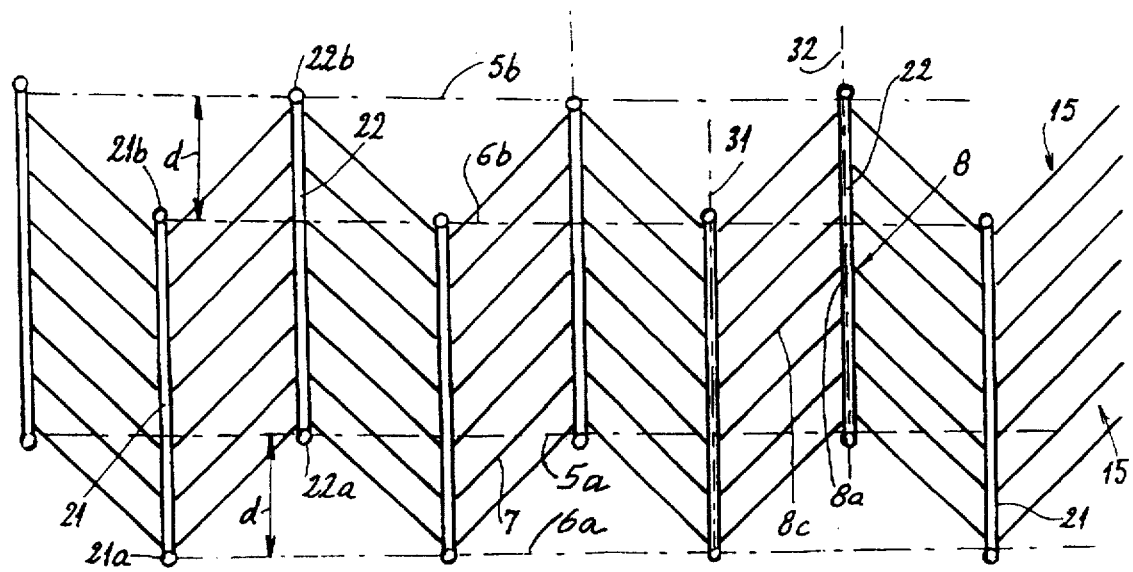
FIG. 3 represents a view, in a development, and from the side, of the endoprosthesis represented in FIGS. 1 and 2.

As is shown more clearly by FIG. 3, the intermediate longitudinal elements 22 are offset longitudinally, or parallel to the axis 3, with respect to the external longitudinal elements 21 by the same predetermined distance (d), in such a way that, at each end 1a or 1b of the endoprosthesis, the extremities 22a or 22b of the intermediate elements 22 are included in a radial plane 5a or 5b separated by the distance (d) from the radial plane 6a or 6b including the adjacent extremities 21a or 21b of the external elements 21.

In a general manner, each ring 15 comprises, along its cylindrical developed surface, 2n transverse strands 7 connected continuously to one another and forming, in pairs, n chevrons 8 whose vertices 8a are linked respectively to the intermediate longitudinal elements 22, and the extremities 8b of the arms 8c are linked respectively to the external longitudinal elements 21. The transverse strands 7 of each ring 15 together have the form of a substantially continuous and closed filament 9, of zigzag configuration, and included in an imaginary envelope of cylindrical shape. The vertices 9a and 9c, respectively, of the salient 9b and reentrant 9d angles of the various rings 15 are aligned respectively along external 31 and intermediate 32 imaginary lines which are parallel to the axis 3 of the endoprosthesis. The chevrons 8 of the various rings 15 respectively are all oriented in the same direction, in such a way that, when the endoprosthesis is viewed from the outside and from the side, one intermediate longitudinal element 22 and all the transverse strands which are connected or attached to it (as defined hereinafter) on either side together exhibit the shape of a fish bone.

As represented more particularly in FIGS. 1 and 4, the filiform longitudinal elements 21 and 22 are intersected by the filaments 9 of the various rings 15 respectively, at the site or at the level of the external 31 and intermediate 32 imaginary lines defined above. The longitudinal filiform elements 21 and 22 and/or the filaments 9 of the various rings 15 are designed to be linked to one another in a definitive position, at the site of their respective intersections 10. To do this, the flexible filiform elements 21 and 22 each consist of a plurality of filaments 11 twisted together, through which the filaments 9 of the various rings 15 pass at the site of their intersections 10.

The structure described earlier presents an inherent centrifugal force of elastic return, on account of the fact that it is the result of the assembly, as it were, of several fish-bone patterns joined to one another via the external and intermediate longitudinal elements 21 and 22.

By longitudinal traction exerted on the external elements 21 with respect to the intermediate elements 22, in the direction of the axis 3 of the endoprosthesis, it is possible to convert the latter from its deployed and released state, in which the internal lumen 4 exhibits a relatively large diameter, to a folded-down configuration, counter to the inherent centrifugal force of elastic return, defined earlier. In practice, this traction can be obtained, for the positioning of the endoprosthesis, using all kinds of devices permitting its introduction into an anatomical channel or conduit, as is represented more particularly in FIGS. 6 through 8 of the document EP-A-0,566,807, the corresponding description of which is incorporated in the present patent application, as and when necessary.

The following modifications or variants are to be made to the construction defined above.

Figure 6:
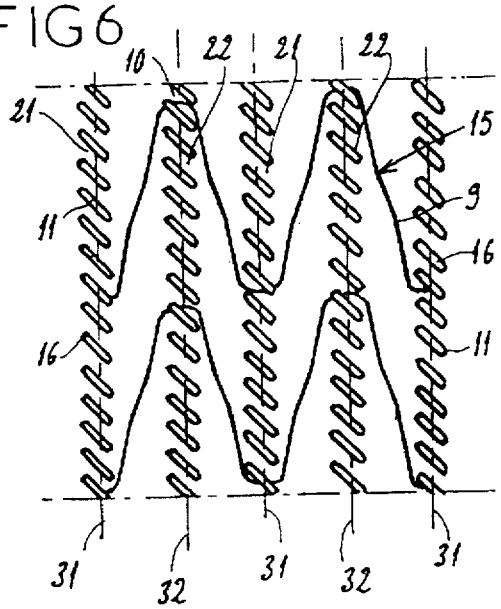
FIG. 6 represents a partial view, in development, from the side, of an endoprosthesis in accordance with a second embodiment of the invention.
Figure 7:
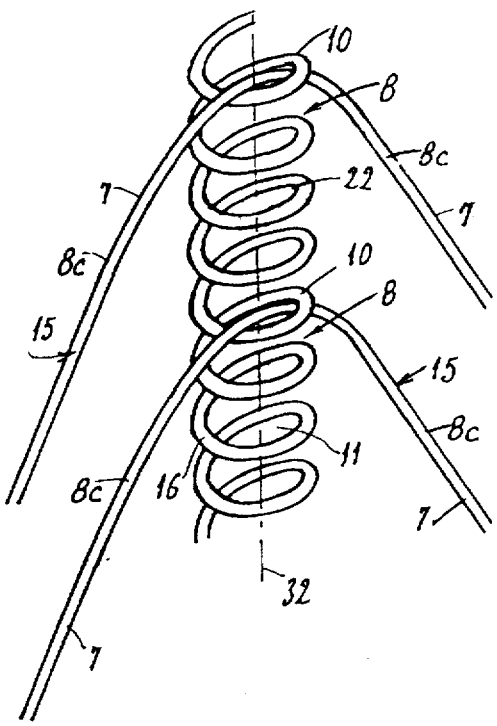
FIG. 7 represents a partial side view, on an enlarged scale, of the prosthesis represented in FIG. 6.

In accordance with FIGS. 6 and 7, the flexible, filiform and longitudinal elements 21 and 22 each consist of at least one helical filament, in such a way that, at the site of their intersections 10, the filaments 9 of the various rings pass through and are held by the coils 11. The filiform elements 21 and 22 can be obtained by combining at least two inverted coils which are assembled on one another.

In accordance with the representation in FIG. 3, the extremities 21a, 21b, 22a and 22b of the flexible filiform elements 21 and 22 are rounded, for example as an end having the shape of a bead.

Figure 8:
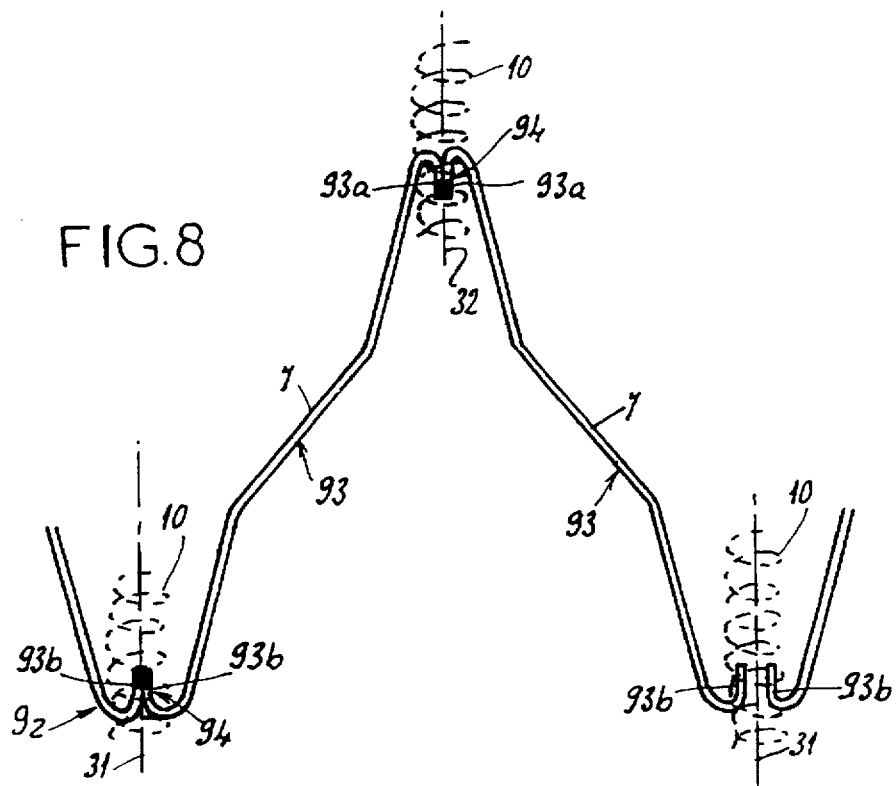
FIG. 8 represents a partial side view of a ring, formed according to another embodiment of the invention, and belonging to an endoprosthesis according to FIG. 7.

Several different procedures can be employed to obtain each zigzagged ring 15:

a section of wire can first be shaped into a zigzag, the two extremities of which are then joined to each other, for example by welding;

in accordance with FIG. 5, a plurality of sections 91 can also be cut from wire, which sections 91 are then shaped to form chevrons; and these chevrons are connected to one another so as to form a closed zigzagged ring 15, for example by welding the contiguous extremities 8b of the chevrons 8 placed alongside one another, with their respective vertices oriented in the same direction;

in accordance with FIG. 8, the filament 9 of each ring 15 is obtained by cutting from a filament, for example a wire, a plurality of half-sections 93 each configured as a half chevron, by connecting the half sections to one another in such a way as to form complete chevrons which are connected to one another in such a manner as to form a closed zigzagged ring 15, and this being done, for example, by welding 94 the contiguous extremities 93a, 93b, placed alongside one another, with the respective vertices of the chevrons 8 oriented in the same direction.

The vertices 9a and 9c of the zigzagged rings 15 can be flattened and oriented perpendicular to the axis 3 of the endoprosthesis.

In order to confer still more flexibility on the endoprosthesis, in accordance with the representation in FIG. 5, the arms 8c of the zigzagged rings 15 each have two obtuse angles 8e and 8f, one reentrant and the other salient.

I claim:

1. A self-expanding endoprosthesis for supporting a wall of an anatomical channel, being of a generally cylindrical form and of openwork design, forming an internal lumen, and being capable of assuming two configurations, a first configuration in which it is folded-down counter to an inherent centrifugal force of elastic return of the endoprosthesis, and in which the internal lumen exhibits a relatively small diameter, and a second configuration in which it is deployed, released under the effect of said centrifugal force, and in which the internal lumen exhibits a relatively large diameter, said endoprosthesis comprising:

n external longitudinal elements, distributed in a parallel arrangement about a longitudinal axis of the endoprosthesis;

n intermediate longitudinal elements, distributed in a parallel arrangement about the axis of the endoprosthesis, each intermediate longitudinal element being between a respective pair of the external longitudinal elements, n being an integer and the total number of longitudinal elements being 2n;

the intermediate longitudinal elements being offset longitudinally with respect to the external longitudinal elements by a predetermined distance, in such a way that, at each end of the endoprosthesis, adjacent extremities of the intermediate elements are included in a radial plane separated by said predetermined distance from a radial plane including adjacent extremities of the external elements;

a plurality of rings distributed along the axis of the endoprosthesis, joining the external and intermediate longitudinal elements to one another, each ring comprising 2n transverse ring segments connected continuously to one another, each ring segment having first and second ends, the first ends of the ring segments being linked respectively to the intermediate elements, and second ends of the ring segments being linked respectively to the external elements;

the folded-down configuration being obtained by longitudinal reaction of the external elements, with respect to the intermediate elements, in the direction of the axis of the endoprosthesis, wherein the plurality of rings are separate from one another, and are linked movably to the external and intermediate longitudinal elements;

wherein the respective ring segments of each ring together have the form of a continuous and closed filament, of zigzag configuration, and included in an imaginary envelope of the endoprosthesis, the zigzag configuration of the rings defining vertices, the vertices of each ring being aligned and nested with the vertices of each adjacent ring, in a longitudinal direction which is parallel to the axis of the endoprosthesis;

wherein at least some of said longitudinal elements are flexible, filament-shaped elements.

2. The endoprosthesis as claimed in claim 1, wherein the flexible filament-shaped elements each comprise a plurality of twisted filaments through which the filaments of the rings pass at their respective intersections.

3. The endoprosthesis as claimed in claim 1, wherein the flexible filament-shaped elements comprise, at the site of their intersections with the rings, coils through which the filaments of the rings pass.

4. The endoprosthesis as claimed in claim 1, wherein the flexible filament-shaped elements each comprise at least one helical filament.

5. The endoprosthesis as claimed in claim 1, wherein the extremities of the flexible filament-shaped elements are rounded.

6. The endoprosthesis as claimed in claim 1, wherein each ring segment of each ring is a separate filament, joined at its extremities to each adjacent ring segment.

7. The endoprosthesis as claimed in claim 1, wherein each ring is formed by a plurality of chevron-shaped filament sections each comprising a respective pair of ring segments, and connected to one another so as to form said closed zigzagged ring.

8. The endoprosthesis as claimed in claim 1, wherein each ring is formed by a plurality of filament-shaped half-sections, each configured as a half-chevron, and connected to one another to form complete chevrons which are connected to one another to form said closed zigzagged ring.

9. The endoprosthesis as claimed in claim 1, wherein the vertices of the rings are flattened.

10. The endoprosthesis as claimed in claim 1, wherein each ring segment has two obtuse angles defined therein, said two angles being oriented in generally opposite direction with respect to the longitudinal axis of the endoprosthesis.

* * * * *